US010078071B2

(12) United States Patent
Alborn et al.

(10) Patent No.: US 10,078,071 B2
(45) Date of Patent: Sep. 18, 2018

(54) TECHNIQUE FOR THERMAL DESORPTION ANALYSES OF THERMO LABILE VOLATILE COMPOUNDS

(71) Applicant: The United States of America, as Represented by the Secretary of Agriculture, Washington, DC (US)

(72) Inventors: Hans T. Alborn, Gainesville, FL (US); Steven D. Willms, Alachua, FL (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 275 days.

(21) Appl. No.: 14/869,984

(22) Filed: Sep. 29, 2015

(65) Prior Publication Data

US 2016/0103102 A1   Apr. 14, 2016

Related U.S. Application Data

(60) Provisional application No. 62/056,953, filed on Sep. 29, 2014.

(51) Int. Cl.
*G01N 30/12*   (2006.01)

(52) U.S. Cl.
CPC ....... *G01N 30/12* (2013.01); *G01N 2030/122* (2013.01)

(58) Field of Classification Search
CPC ............. G01N 30/12; G01N 2030/121; G01N 2030/122; G01N 2030/128; G01N 2030/025

See application file for complete search history.

(56) References Cited

U.S. PATENT DOCUMENTS 6,311,544 B1 * 11/2001 Bertrand ................ G01N 30/30
210/198.2

OTHER PUBLICATIONS

Article titled "A Micro-Preparative Gas Chromatograph and a Modified Carbon Skeleton Determinator" by Brownlee et al. publised Nov. 1968.*

* cited by examiner

*Primary Examiner* — Blake A Tankersley
(74) *Attorney, Agent, or Firm* — Ediz Yonter; John Fado

(57) ABSTRACT

Herein is described an apparatus for adaptation to existing GC/MS systems, utilizing a splitless injector as the desorption oven with a liquid $CO_2$ cooled low thermal mass cryo trap that eliminates the need for flash heating of volatile compounds.

1 Claim, 13 Drawing Sheets

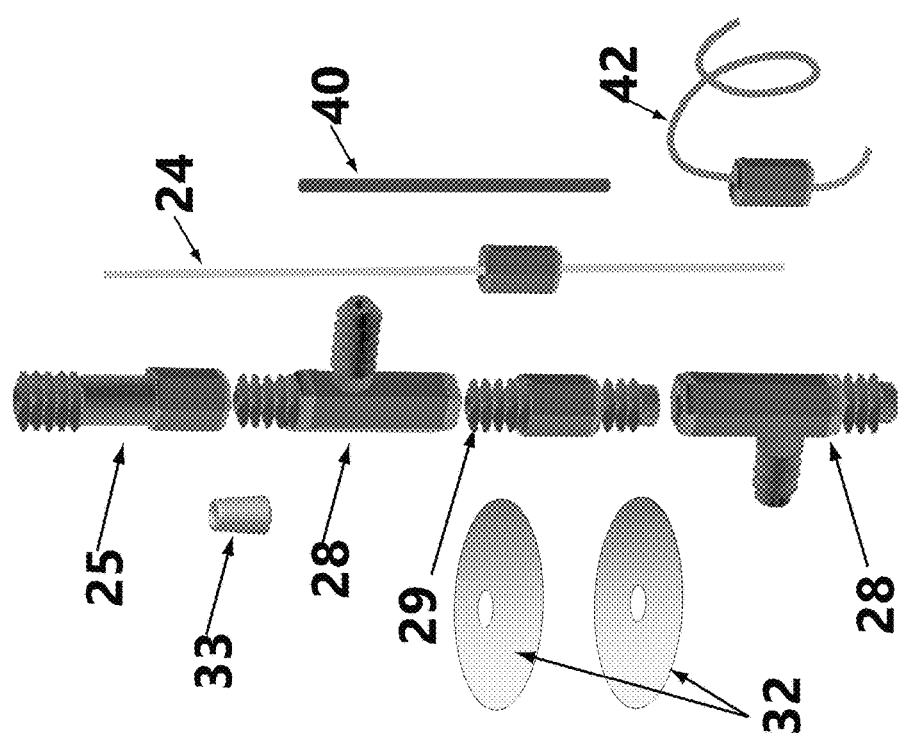

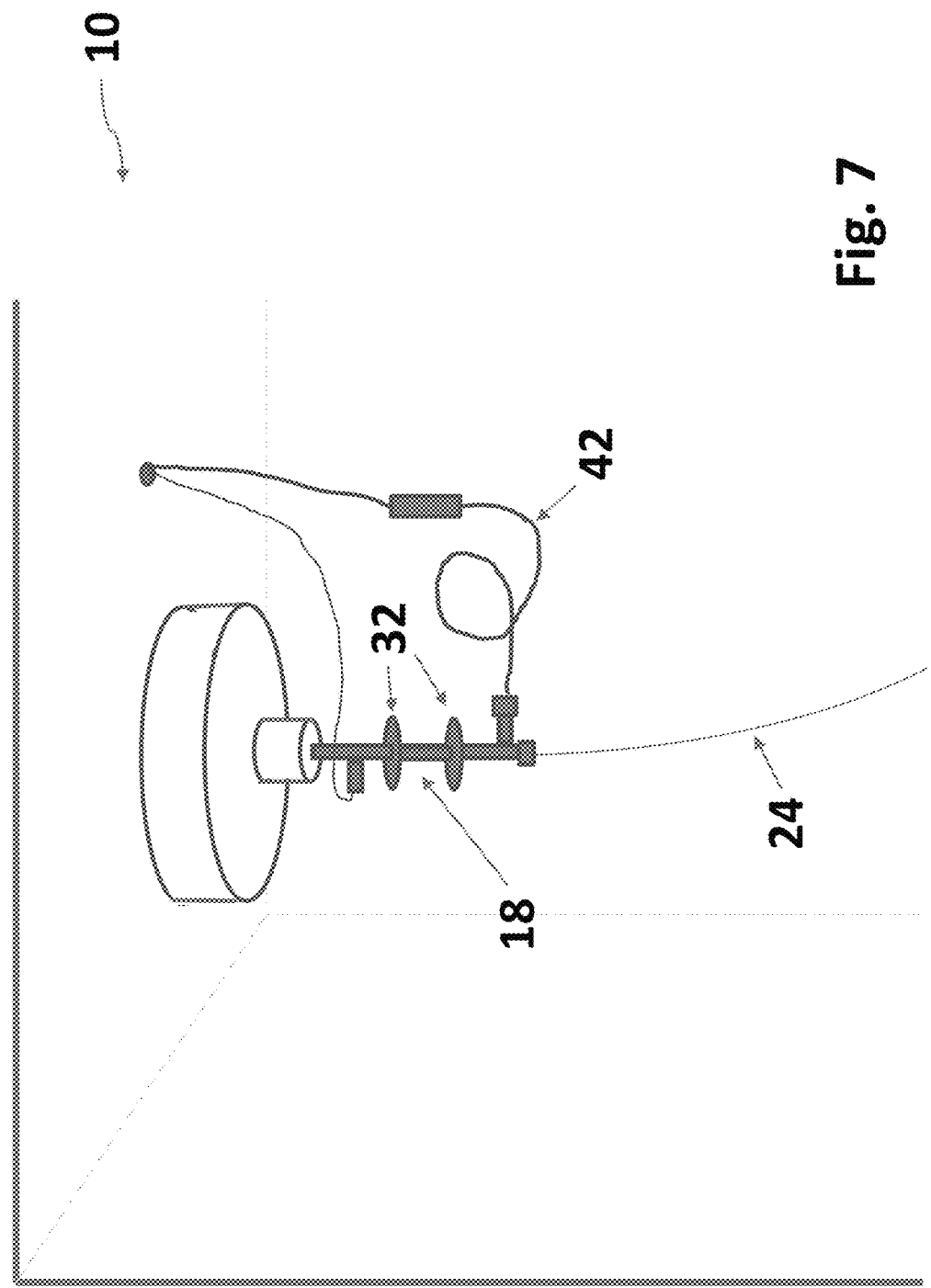

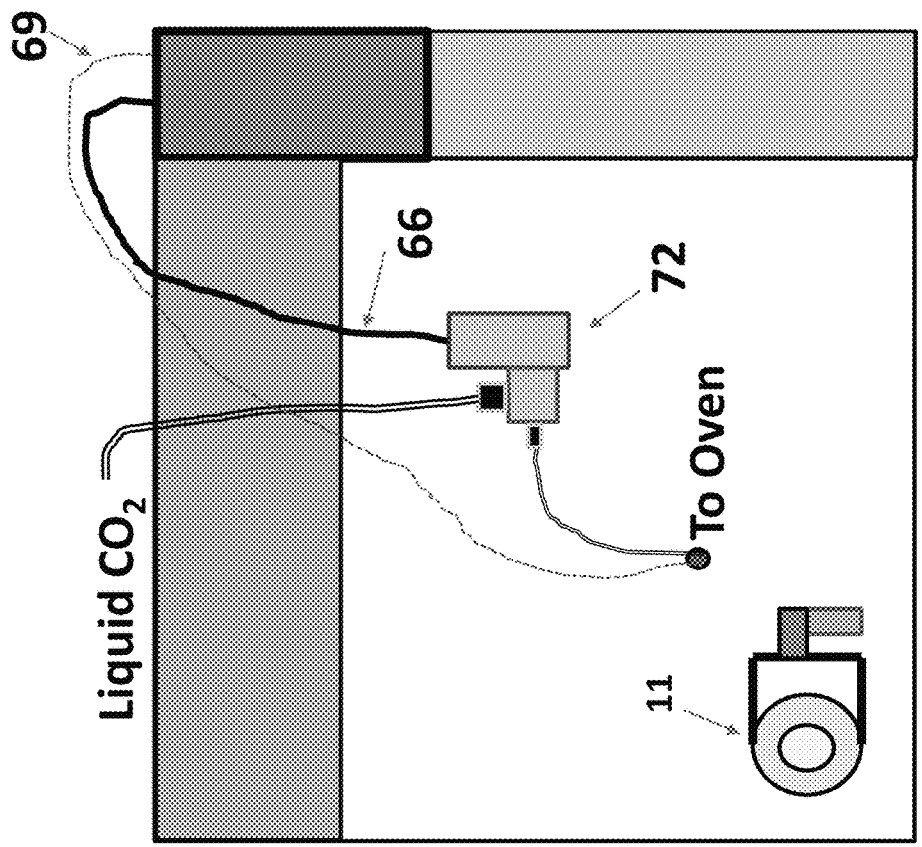
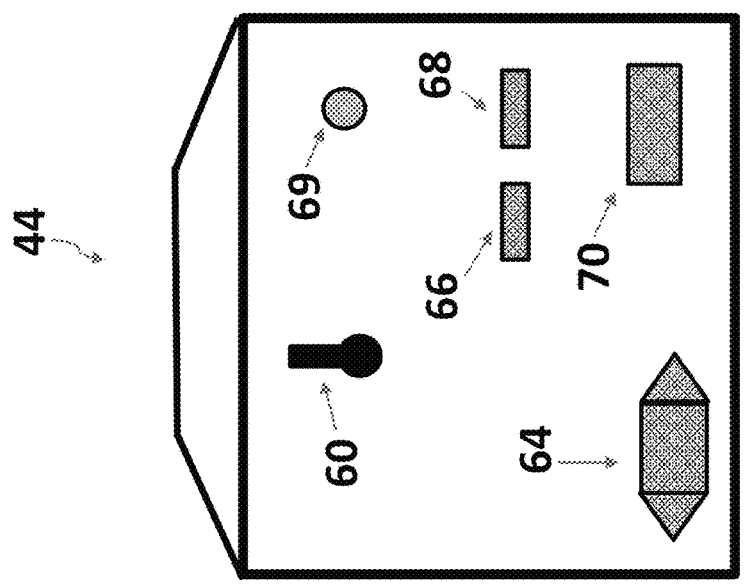
Fig 12B
Fig 12A

TECHNIQUE FOR THERMAL DESORPTION ANALYSES OF THERMO LABILE VOLATILE COMPOUNDS

RELATED APPLICATIONS

This application claims the benefit of priority of U.S. Provisional Application No. 62/056,953, filed on Sep. 29, 2014, which is herein incorporated by reference in its entirety for all purposes.

FIELD OF THE INVENTION

The invention relates to apparatus and methods for analysis of volatile organic compounds in a gas chromatogram thermal desorption system and more particularly to a system having a cryo trap directly attached to a split/splitless injector and a means of transferring the desorbed compounds from an injector to the top part of a chromatographic column.

BACKGROUND OF RELATED ART

Many interactions in nature are governed by volatile compounds released by, for example, plants or insects. The power of these compounds to affect the behavior of phytophagous insects, has led to a need for methods to collect and identify them. The most commonly utilized technique relies on adsorption of the volatile compounds on a polymer like SuperQ, charcoal or Tenax which then are extracted with a solvent to release the compounds. The extracts are typically analyzed by GC/MS utilizing split/splitless or on column injection. The main problems with this technique are that the extraction step dilutes the sample which makes it necessary to collect for a relatively long time, typically from 1 to 24 hours or to use more material releasing the volatile compounds. However, in a natural situation, for example, the release of leaf volatiles or insect pheromones, the volatile organic compounds might be released during a short or specific time period or the pattern of the volatiles might change over time, thus long time collections might result in a mixed sample that does not mimic a natural blend. Furthermore, increasing the source releasing the volatiles might not result in the desired increase of release. For example, the release of pheromone by a single insect might be hampered by the presence of more insects or the physical limitation of a collection enclosure limits the amount of plant material that can be contained. The technique of choice for those situations has been to use the adsorbent Tenax 16 that can be desorbed by heat in a technique suitably named Thermal desorption (FIG. 1). With this solvent free injection technique, the filter 16 containing the sample is placed in a specifically designed oven where the volatile compounds are released from the filter 16 by elevated temperature and by a constant flow of a carrier gas such as He into Gas inlet 20. The gas is passing through a trap 19, cold with liquid $CO_2$ or sometimes liquid $N_2$, where the volatile compounds will be retained. After a suitable desorption time the cryo trap 19 is flash heated to release/inject the trapped compounds onto the GC column 24 that is temperature programmed as with a standard solvent injection. The desorption oven 11 as well as the cryo trap 19 might be located in a separate unit outside the gas chromatograph in which case there is a substantial transfer line 14 between the cryo trap 19 and the GC or the cryo trap 19 might be located in the GC oven 11 in which case there might be a transfer line 14 between the desorption unit and the cryo trap. Whenever transfer lines 14 are used, these need to be inert and sufficiently heated to eliminate any unwanted adsorption and/or degradation. The desorption of the Tenax filter 16 creates less of a degradation problem since, for example, sesquiterpenes are totally desorbed in less than 2 minutes at a temperature of 130° C. to 150° C. and temperatures above that are rarely needed. The germacrene family of sesquiterpenes as well as the 12 carbon terpenoid pregeijerene will degrade at temperatures above 150° C. and are typically not degraded by the desorption step while those types of labile compounds rarely survive thermal desorption injection lays due to the design of cryo traps. First, cryo traps are typically evenly cooled leading to aerosol formation at the interface where warm desorption gas is abruptly cooled down to −78° C. (with CO2), or lower. The trap therefore either has to be sufficiently long to trap aerosol droplets or be filled with, for example glass wool, to increase the surface area. To inject a sample onto the column 24, these cryo traps must be flash heated to 200° C. or higher temperatures to eliminate chromatographic peak broadening. This, in combination with active sites in the traps, such as glass wool, is the major source of sample degradation often observed with thermal desorption and very much eliminates its usefulness for natural product analyses.

Thus, what is needed in the art is a new cryo trap 18 that easily adapts to existing GC/MS systems and utilizes existing splitless injectors 11 as a desorption oven to which the cryo trap 18 of the present invention can be easily attached, as will be clear from the following disclosure, the present invention provides for this and other needs.

SUMMARY OF THE INVENTION

It is therefore an object of the present invention to provide a novel thermal desorption system 10 which creates a temperature gradient for more efficient trapping as well as focusing of volatile compounds where the later in combination with low thermal mass eliminates the need for a flash heating injection step.

Another object of the invention is to provide a novel thermal desorption system 10 with low thermal mass that can be left in a gas chromatogram oven when not in use that does not require any changes in the oven when switching between thermal desorption and splitless injection and does not affect chromatography when not in use.

A further object of the invention is to provide a novel thermal desorption system 10 which achieves a reduction in aerosol formation by eliminating abrupt temperature changes wherein the entrance of the trap has a temperature close to the desorption oven and then gradually cooled to a maximum cooling near the end of the trap.

A still further object of the invention is a cryo trap control box to control the valve that controls the flow of liquid $CO_2$ going to the apparatus.

Other features, objects and advantages of the invention will be apparent from the detailed description which follows.

BRIEF DESCRIPTION OF THE DRAWINGS

FIGS. 6A and 6B are drawings of the thermal desorption system 10 utilizing aluminum heat sinks 32. FIG. 6A shows the system completely assembled and FIG. 6B shows an exploded view of system 10.

FIG. 7 is an illustration of the System 10 having cryo trap 18 attached to a split/splitless injector 11 with the temperature sensor position at the CO2 exit. The liquid $CO_2$ enters at the bottom right of the trap 18 and the restrictor 42 tubing can easily be adjusted very close to the GLT tubing 40 (not shown-See FIG. 6A and FIG. 6B) inside the trap 18. An approximately 0.53 mm fused silica tubing 42 housed inside the GLT tubing 40 exits at the bottom of the trap 18 where the cap functions as a gas tight seal and also allows for an easy exchange of the GLT tubing 40 without taking apart the trap 18. FIG. 7 shows the connection between the approximately 0.53 mm tubing 42 inside the trap 18 and an approximately 0.22 mm ID analytical GC column 24 through the use of a fused silica connector (Supelco #23628). The approximately 0.53 mm tubing 42 and column 24 have the same stationary phase and film thickness.

FIG. 11A shows the temperature display 45 and indicator lights 46. FIG. 11B shows circuit card 48 with 2 relays 50.

FIGS. 12A and 12B show the rear of control box 44. FIG. 12A shows the power out to relay 50,

DEFINITIONS

Figure 1:
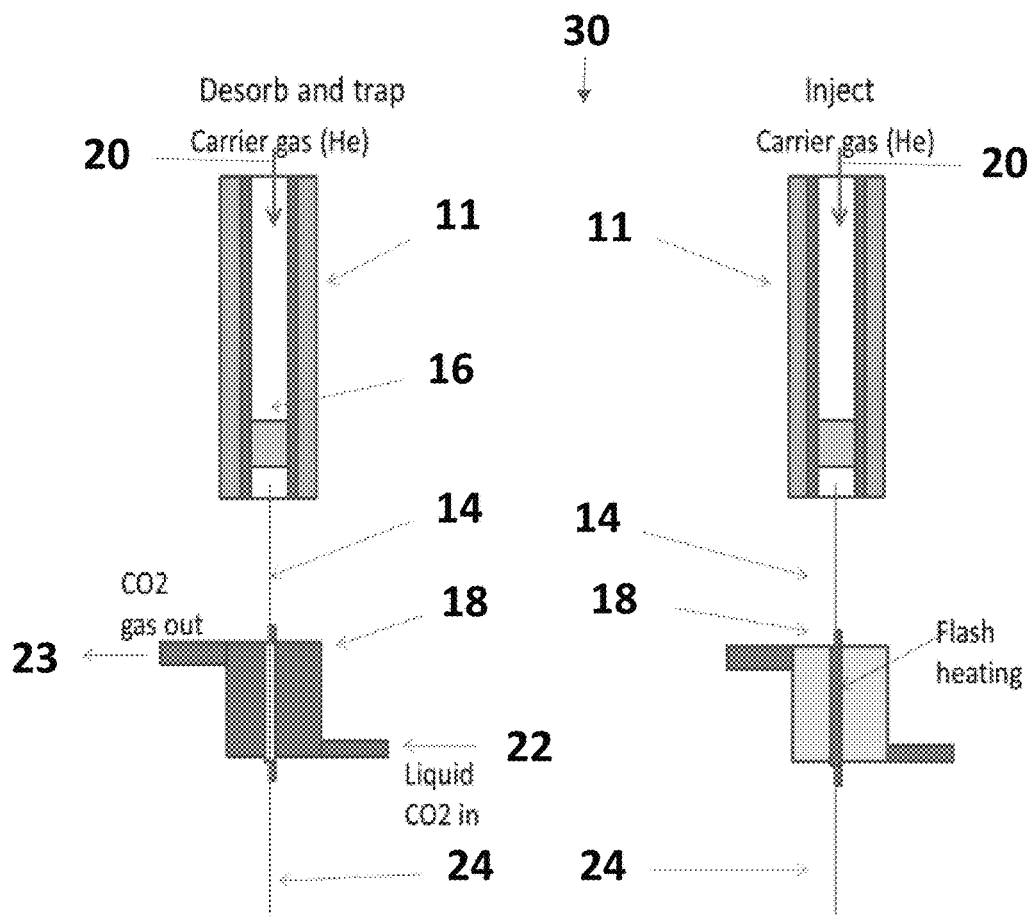
FIG. 1 is a schematic of a typical prior art system 30.

As used herein the term "thermal mass" is a material resistance to change in temperature as heat is added or removed. Thus an apparatus located in a GC oven and being part of the chromatographic system needs low thermal mass in combination with efficient heat exchange with the circulating air as to closely follow rapid (5 to 10 C/min) changes in temperature of the oven.

As used in the specification and claims, the singular form "a", "an" and "the" include plural references unless the context clearly dictates otherwise. For example, "a cryo trap 18" includes a plurality of the same cryo trap 18.

As used in the specification and claims, the terms "about" and "approximately" mean to be nearly the same as a referenced number or value. As used herein, the terms "about" and "approximately" should be generally understood to encompass ±10% of a specified amount, frequency, or value. Further, all numbers expressing the quantities used in the specification and claims for example, concentrations, reaction times, reaction conditions, temperature, and yield, are modified by the term "approximately" unless otherwise indicated. As used herein when a numerical range is given, both ends of the range are included.

The term "substantial" or "substantially" mean of real worth or importance, or considerable value. For example, a substantial increase or decrease means a change greater than 5% of the previously measured value.

DETAILED DESCRIPTION OF THE INVENTION

The most sensitive of available techniques to study volatile compounds in natural systems is adsorption on the polymer Tenax and direct injection by thermal desorption onto a GC/MS. This solvent free injection technique, that utilizes a desorption oven and a cryo trap 19 as in FIG. 1, System 30, where effluents are collected until flash heated onto the GC column 24, is rarely utilized in natural product chemistry since commercially available systems are complex and expensive and the repeated heating as well as the use of transfer lines 14 result in degradation of labile compounds. It is also often necessary to dedicate a GC/MS system for thermal desorption, increasing the cost further. The invention as shown in FIGS. 5, 6A, 6B, and 7, eliminates most of these problems, first by being designed as an integral part of a standard split/splitless GC injector 11 which is used as the desorption oven but still can be used as a normal injector 11 without any additional changes. Second, the cryo trap 18 eliminates losses due to aerosol formation by utilizing a temperature gradient which also focuses the effluent, eliminating the need for flash heating. Heat exchanged from the circulating air in the GC oven in combination with 2 aluminum heat exchangers 32 and low thermal mass makes any additional heating unnecessary. The performance mimics what typically is achieved with very gentle solvent based cool on column injection, which until now was the only available injection technique for labile samples.

Research on interactions governed by volatile chemistry often requires collection and analyses of trace volatiles found, for example, in soil or locations such as within bee hives or glands of individual insects. Success often depends on the ability to take snap shots rather than long time accumulations that all but eliminates the possibility to monitor the release from any single or dynamically changing source. In those situations, thermal desorption is the technology of choice. However, the serious limitations mentioned above made it necessary to develop and improve on thermal desorption, such as the present invention, as an injection system 10 (FIG. 5, FIGS. 6A and 6B, FIG. 7). Herein is described an apparatus which overcomes limitations in the prior art efficient trapping as well as focusing of volatile compounds utilizing (1) simple design and ease of adaptation to existing GC/MS systems, (2) existing splitless injector 11 as a desorption oven 11: An injector 11 is uniformly heated, has exact temperature control, has exact and adjustable carrier gas flow and a split valve that can be used to cut off "the tail". Thus many injectors 11 can be fit with a tool free top for quick change of insert, (3) an adsorption filter 16 that fits in the injector 11 housing: based on or dimensioned after standard injector 11 inserts, (4) a low thermal mass cryo trap 18 that can be left in GC oven when not in use that does not require any changes in the oven when switching between thermal desorption and splitless injection and does not affect chromatography when not in use, (5) a reduction in aerosol formation by eliminating abrupt temperature changes wherein the entrance of the trap 18 has a temperature close to the desorption oven and then gradually cooled to a maximum cooling near the end of the trap 18, the design should be close to that of preparative GC fraction collectors (Brownlee, R.; Silverstein, R. M. *Anal. Chem.* 1968, 40, 2077-2079) that were designed specifically to deal with aerosol formation by using a temperature gradient, (5) a focusing step to minimize peak broadening: the above temperature gradient maintained during the heating step should preserve the focusing achieved with the cooling gradient, thus no flash heating of the whole cryo trap 18 is necessary (6) optimization of trap 18 length, since a short trap 18 can result in insufficient trapping and a long trap 18 can result in broad peaks for very volatile compounds (7) reduced thermal degradation wherein the desorbed sample deposited in the column 24 within the trap 18 catalytic surfaces can be eliminated; a gradual heating of the column, as with cool on column injection, resulting in a similar reduction in degradation; with low thermal mass the circulation of hot air in the GC oven should be enough to increase the temperature of the trap 18, especially if additional heat can be added from the heated injector oven 11, (8) minimization of risk of cold spots that will result in peak tailing, thus resulting in no excess material and minimization of the use of $CO_2$. Thus with only a small part of the cryo trap 18 at minimum temperature, substantially less liquid CO2 should be needed than in traditional cryo traps 19.

The scope of the invention is a thermal adsorption system 10 having cryo trap 18 add-on to a standard split/splitless injector 11 which is utilized as a desorption oven for the collection filters 16. An original column nut 25 for the injector 11 has been threaded on the inside so that the rest of the cryo trap 18 can be easily attached to it. The empty space within the nut 25 has been filled with a piece of form fitted copper or brass insert 38 with a hole drilled to fit the GLC tubing 40 which is the housing within the trap 18 for a section of fused silica capillary column on which the desorbed sample will be trapped. Straight glass lined tubing (GLT) 40 is available that fit any dimension of fused silica capillary column but other straight steel tubing will work as well. The insert 38 maximizes the heat transfer from the injector 11 to the top part of the GLT tubing 40 housing the chromatography column. The column can be of any dimension but a piece of large bore 0.53 mm ID inside the tubing in the cryo trap 18 gives highest sample capacity and reduces the risk of ice clogging the column. The tubing is housed inside the trap 18 constructed by GC fittings 28 and 29 that have been drilled out internally to approximately 1.85 mm ID to allow a flow of CO2 in a bottom to top direction, thus when combined with the heat applied form the top, forms a temperature gradient over the GLT column housing tube.

A key embodiment of the cryo trap 18 is the temperature gradient established in part by the narrowing of the inner diameter of the liquid CO2 tubing wherein the narrowing diameter functions as a restrictor 42 forcing the CO2 pressure drop and consequently maximum cooling to occur at the end of the restrictor 42 only. The differential of focused cooling with applied heating (FIG. 5) minimizes the risk of aerosol formation and cold spots that will result in incomplete trapping, broad or tailing chromatographic peaks and minimizes the use of CO2, wherein only a small part of the cryo trap 18, at minimum temperature, is necessary. Although as described herein, the last approximately 5 cm of the restrictor 42 portion of the liquid CO2 tubing has an inner diameter of approximately 0.05 mm, one of skill in the art would understand that the length of the restrictor 42 portion would be adjusted proportionally based on the total length of the liquid CO2 tubing.

Another embodiment of the invention is the reduction in thermal mass. The use of a temperature gradient for more efficient trapping as well as focusing of volatile compounds where the later in combination with low thermal mass eliminates the need for a flash heating injection step. Desorption of a Tenax filter 16 depends on a combination of heat, time and flow of desorption gas. The efficiency of the invention makes it possible to avoid degrading of labile compounds simply by increasing desorption time while reducing the heating as needed. Desorption temperatures may range from approximately 50° C. to approximately 200° C. About a 2 minute desorption can typically be carried out at approximately 150° C. and based on preliminary experiments it doesn't appear to be necessary to ever increase the temperature above approximately 200° C. to desorb volatile organic compounds produced and released by live plants or insects. Lower temperatures, down to approximately 50° C. in combination with extended desorption time, up to about 5 minutes, can be used for analyses of very volatile compounds such as common solvents like methanol, ethanol and other but heavier compounds, such as sesquiterpenes which during those conditions will not be completely desorbed from the collection filter 16.

Interfacing with a Gas Chromatograph.

Since the system 10 is designed as an integral part of a gas chromatograph, also the methods of the instrument need to be adapted for use with the trap 18. However, one benefit of the invention is that when the GC isn't used for thermal desorption the only necessary procedure is to load a normal method for split/splitless injection and no physical alterations are necessary. Similarly, switching to a cryo trap 18 method is the only necessary procedure to prepare the system 10 for thermal desorption.

Control Box Design

A cryo trap 18 control box 44 (FIGS. 11A and 11B and FIGS. 12A and 12B) was designed to control the valve 72 that controls the flow of liquid $CO_2$ going to the cryo trap 18 via signals from the GC prep run key and start key on the GC front panel. In addition, the box also utilizes a remote ready signal to prevent any cooling of the trap 18 unless the whole system is ready.

The control box 44 is designed with three light emitting diodes, indicator lights 46, on the front panel that can be used to monitor system status and a cryo trap 18 temperature display 45. Looking left to right on the front of the control box, the first LED indicator light 46 illuminates when the control box 44 receives a ready signal from the GC. The second LED indicator light 46 illuminates when the control box 44 receives a start signal from the GC. The third indicator light 46 LED illuminates when 120 vac is sent to open the CO2 valve and begin cryo trap 18 cooling. The cryo trap 18 temperature display 45 illuminates and displays the actual cryo trap 18 temperature measured at the CO2 outlet 23 when power from the control box 44 on\off switch is turned on.

On the back panel of the control box 44 there is an AC main power connector 64, cryo valve control connector 66, GC Remote connector 68, the thermo coupler temperature sensor connector 69, and a GC External Event connector 70. Located on the back panel there is also switch S2 60 which is a cooling override switch for maintenance and testing purposes. Inside the control box 44 there is a simple circuit card 48 with two diodes and two switching relays 50 and 52 (FIG. 10 and FIG. 11B and FIGS. 12A and 12B).

Control Box Operation.

Figure 11B:
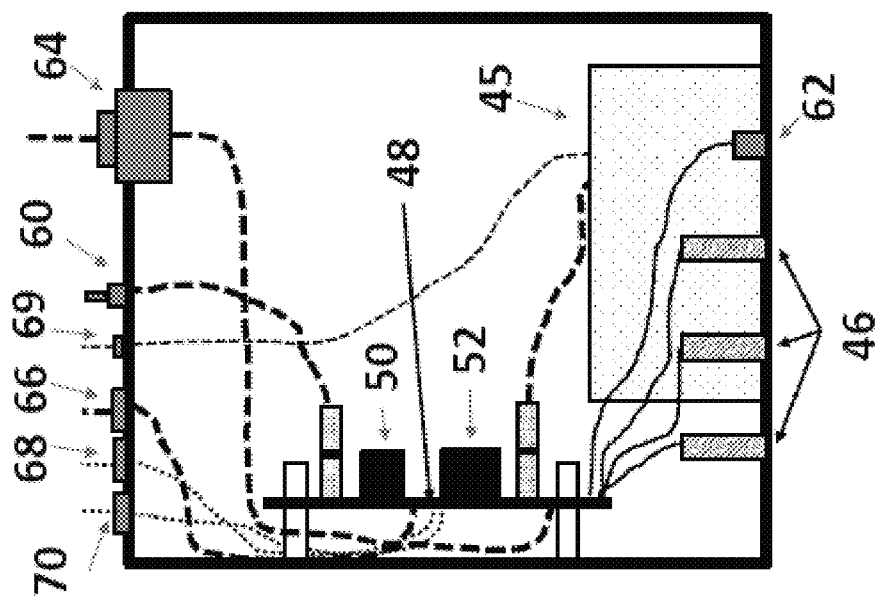
FIGS. 11A and 11B are photographs showing the front (FIG. 11A) and back (FIG. 11B) of control box 44.
Figure 11A:
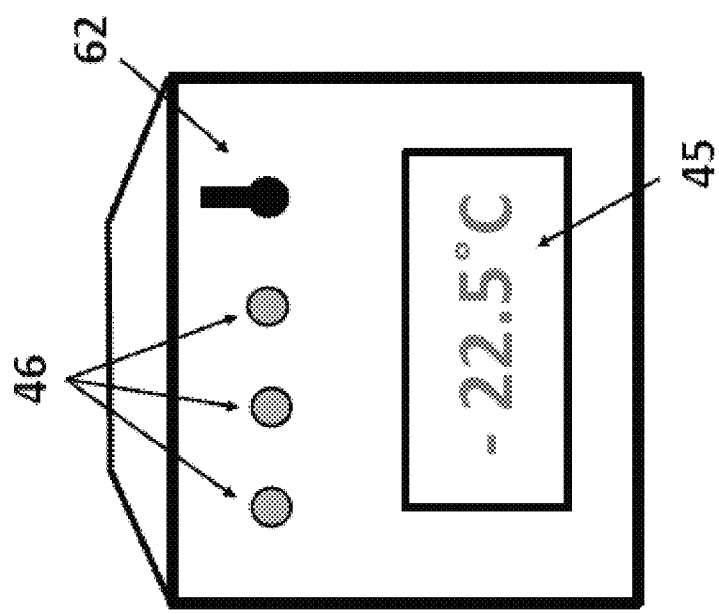

When switch S1 62 is turned on, a 120 vac is routed to the temperature display 45 module which gives a visual indication that the unit is on by displaying the current temperature of the cryo trap 18 within the GC. This 120 vac is also routed to the open side of relay 52 K2 (FIG. 11B). After loading a properly configured cryo trap 18 method and pressing the "Prep Run" key on the front panel of the GC, the pressure of the split/splitless inlet will begin to drop to zero. When the pressure of the injection port reaches zero, and if all other GC set parameters have been met, a "GC ready" signal will be sent out through the GC Remote cable to J2 of the control box 44. This GC ready signal is a +2.2 vdc high that is sent to the positive side winding of relay 50 K1. Because of the ground signal that is always present on the negative side winding, the relay 50 activates. When relay 50 K1 activates, 24 vdc that is always present from the GC External Event connection, is relayed to the Ready LED D3 and through diode D2 to the positive side winding of relay 52 K2 Because of the ground signal that is always present on the negative side winding of relay 52 K2, the relay activates. When relay 52 K2 activates 120 vac is relayed to the Cooling LED D5 and out of the control box 44 to the cryo valve. The cryo valve opens and allows liquid CO2 to be sent to the cryo trap 18 attached to the split/splitless injection port, cooling the trap 18 to approximately −70 degrees Celsius.

When the temperature on the cryo trap 18 control box 44 display reaches the desired temperature (typically −10° C.), the top of the injector 11 port is opened, preferably, a flip top cap, the standard glass insert, or a previously analyzed Tenax filter 16, is removed and the filter 16 to be analyzed is dropped in (touching the filter 16 with bare hands will result in serious background problems), then close the flip-top cap sealing the injection port and press "Start". This turns the carrier gas back on and the "Ready" signal from the GC is removed. Normally, the removal of the ready signal would stop the cooling process of the cryo trap 18. However, with valve #7 set to turn "on" at time 0:00 in the method it creates an electrical short between pins #5 and #6 of the GC External Event Connector, J1. This short allows 24 vdc, which has always been routed from the GC Ext Event connection J1, pin #1 trough the printed circuit board in the control box 44 and back out to J1, pin #5, to be routed through the now closed valve #7 to J1, pin #6 of the control box 44. This 24 vdc is then routed to the Start LED, D4 and through diode D1 to the positive winding of relay 52 K2. Again, because of the ground signal that is always present on the negative side winding of relay 50 K2, the relay activates. When relay 52 K2 activates 120 vac is relayed to the Cooling LED D5 and out of the control box 44 to the cryo valve. This allows the cryo valve to remain open and liquid CO2 to be sent to the cryo trap 18. At runtime 2:00 valve #7 will open up, removing the 24 vdc from relay 52 K2, and thus stopping the cooling process. Simultaneously, gas flow to the split vent at 40 ml/min begin at runtime 2:00. The cryo trap 18 will then begin to warm up and reach the temperature of the oven within a minute.

Gas Chromatograph Method Setup

The described method setup is for Agilent ChemStation software for cryo trap 18 operation with the control box 44 but should be easy to adapt to any reasonably modern GC. Under Edit Method Setup the following changes must be made:

1. Valves Tab

Configure Valve 7 as other.

Do not place a check in the check box for valve #7 on.

2. Inlet Tab

Mode "Pulsed Splitless"

Injection Pulse "0.00 psi until 0.01 min". This assures the carrier gas set to 0 when "prep run" is depressed and that the gas flow resumes when "start" is depressed.

Purge Flow to "Split Vent 40 ml/min @ 2 min". Everything on Tenax filter 16 not desorbed in 2 min will be vented away.

3. Runtime Tab

| Time | Specific | Parameter | Set point |
| --- | --- | --- | --- |
| 0 | Valve | 7 | On |
| 2 min | Valve | 7 | Off |

This sets the desorption time to 2 minutes. Extending or shortening this time need a corresponding change of time for opening of split valve and change of initial isothermal period in GC temperature program.

The following examples are intended only to further illustrate the invention and are not intended to limit the scope of the invention which is defined by the claims.

Example 1

Figure 2:
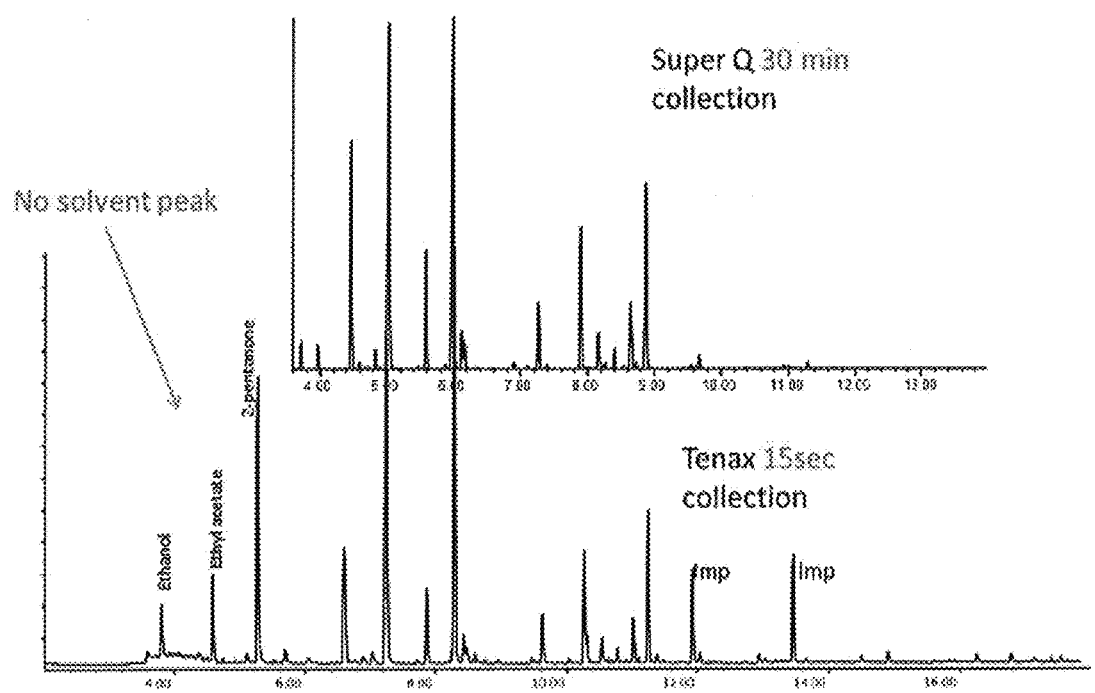
FIG. 2 is a chromatogram of banana fruit volatiles collection on Super Q with solvent extraction versus collection on tenax with thermal desorption injection as illustrated in FIG. 1.
Figure 3:
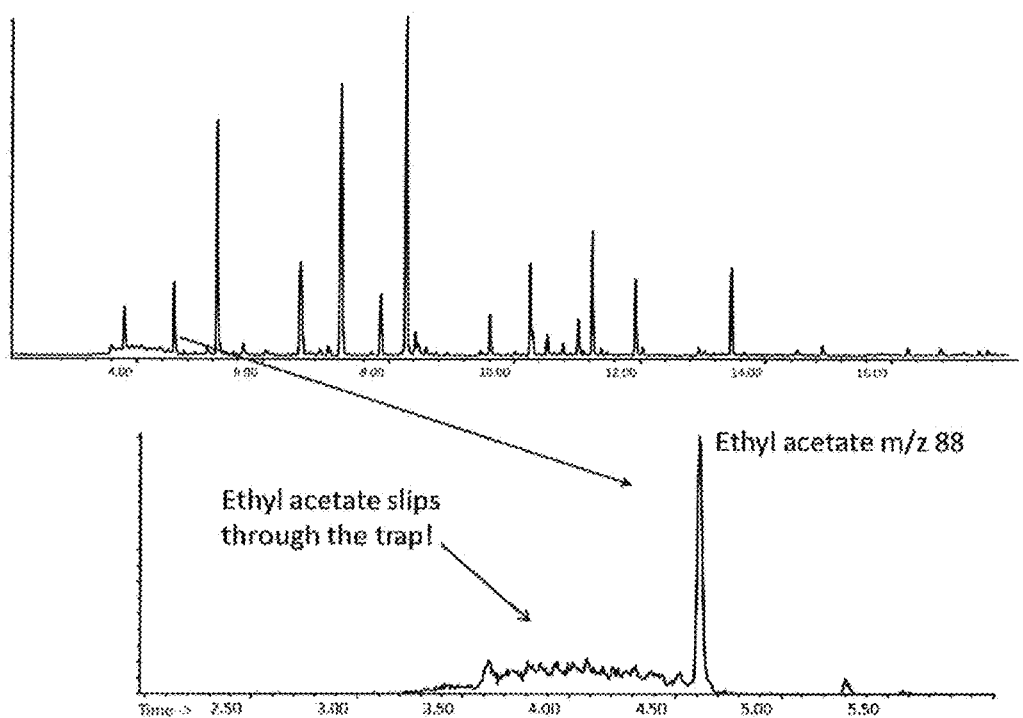
FIG. 3 is a chromatogram of extracted ion trace m/z88 for ethyl acetate showing bleeding through the cryo trap 18 using the prior art system 30 of FIG. 1.
Figure 4A:
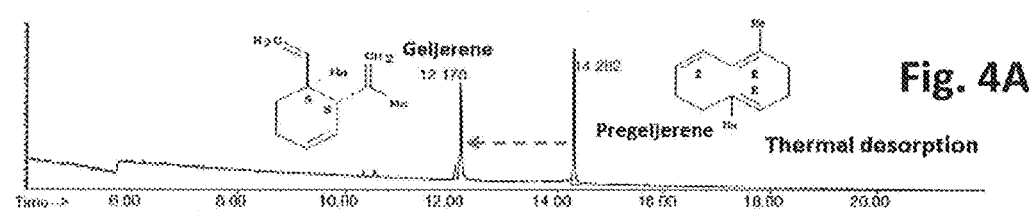
FIG. 4A, FIG. 4B, and FIG. 4C are chromatograms of two minute Tenax (FIG. 4A) and 30 min Super Q (FIG. 4B and FIG. 4C) root volatile collection of potted common rue plants using the system 30 of FIG. 1. Pregeijerene degraded to geijerene when using splitless as well as prior art 30 thermal desorption injections. The additional compounds seen in the SuperQ traces are due to contaminations when air penetrates from above the soil during long collections.
Figure 4B:
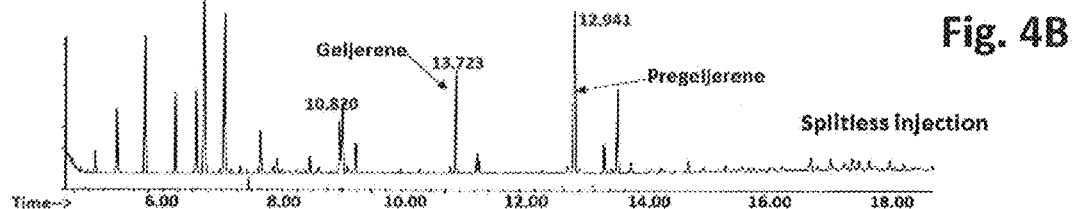
Figure 4C:
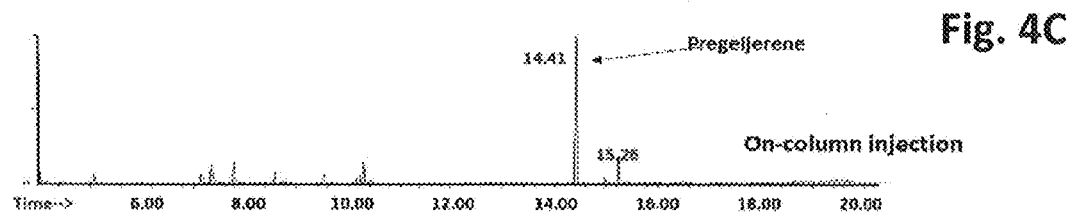
Figure 5:
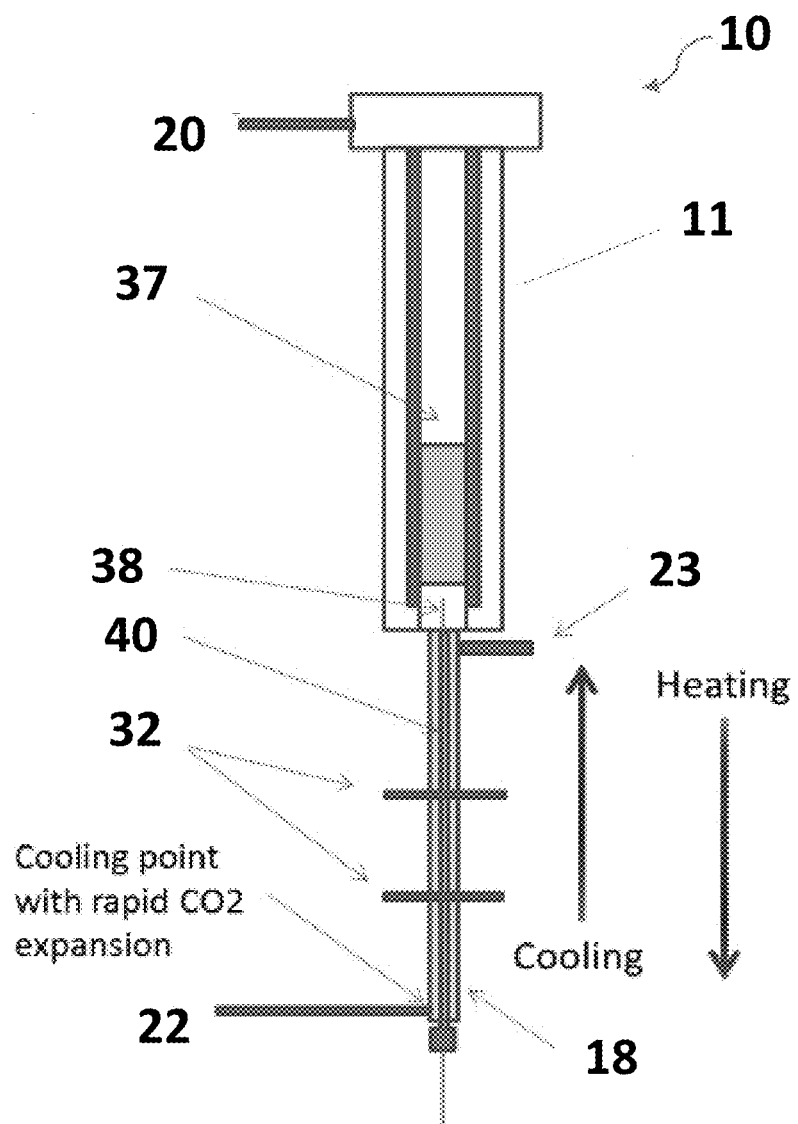
FIG. 5 is a schematic representation of the System 10 having cryo trap 18 housing employed as an add-on to a standard split/splitless injector 11 which is utilized as a desorption oven for the collection filters 16 and where the gas chromatographic carrier gas entering inlet 20 is utilized in the desorption process.
Figure 6A:
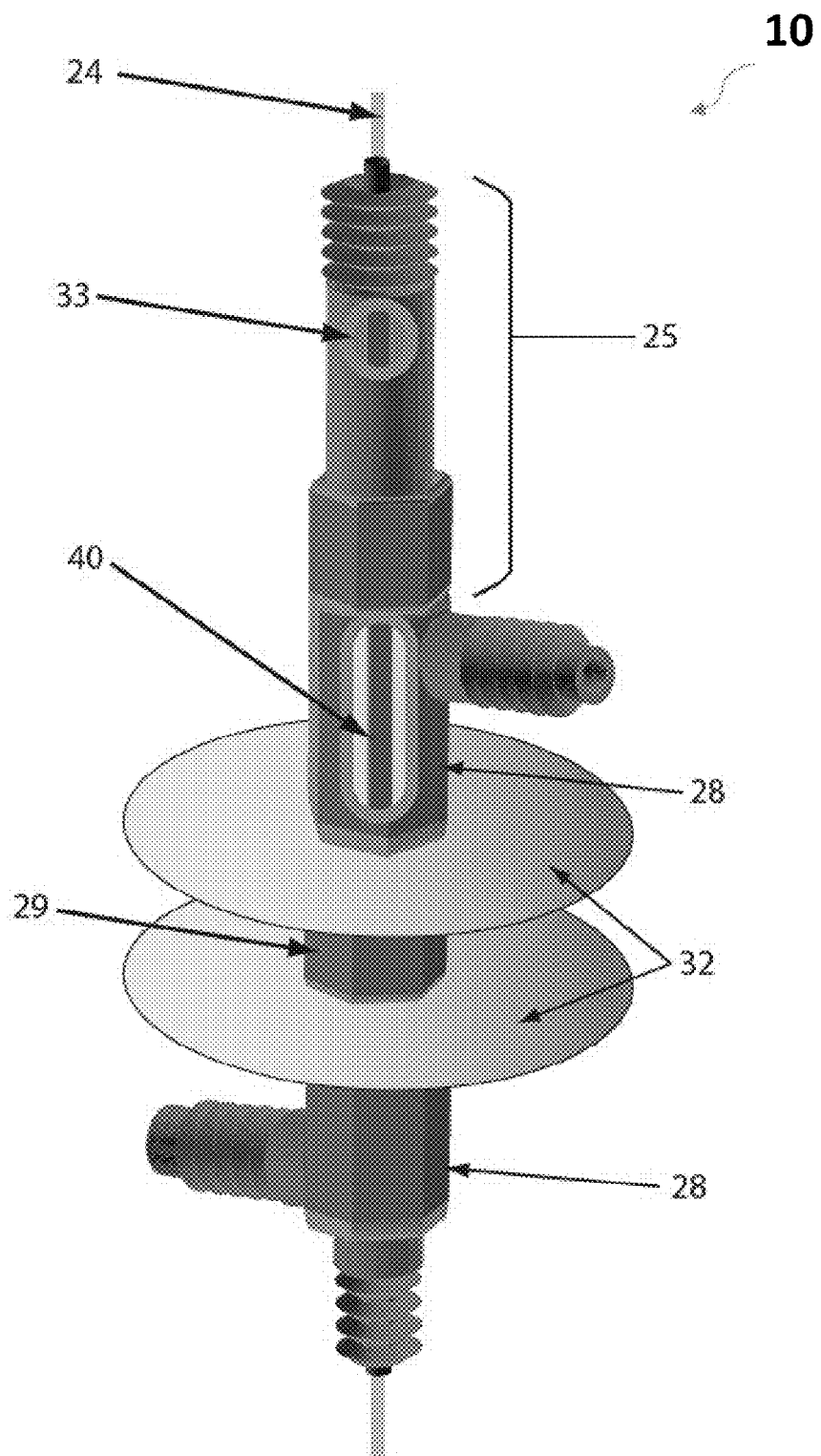

This example compares the use of SuperQ and Tenax which is used in the invention using the related art system 10 shown in FIG. 1 As see in FIG. 2, volatiles were collected from a ripe banana using either a solvent based SuperQ collection or a thermal desorption using Tenax. The same signal to noise ratio was achieved with an about 15 second Tenax collection as compared to an about 30 minute collection on SuperQ where the filter 16 was extracted with 150 µl methylene chloride and 1 µl injected on the GC. The banana was placed in a glass chamber and flushed constantly with clean air at a flow of approximately 200 ml/minute for both collections. With Super Q collection and solvent injection, MS data collection cannot start until the solvent has passed through the GC column 24 and MS, which takes about 3.5 to 4.5 minutes, depending on column length and carrier gas flow. Since no solvent is used with a Tenax collection and thermal desorption, compounds, such as ethanol, and ethyl acetate, FIG. 2, can be detected and quantified. FIG. 3 illustrates one of the problems with standard uniform temperature cryo traps 18 where the abrupt cooling at the entrance to the cryo trap 18 might result in aerosol formation and consequent trap break through as seen in FIG. 3 for ethyl acetate. Another problem with a standard Thermal desorption system 10 is excessive use of heat. Many volatile compounds, especially natural products, are labile and easily degrade with high temperatures. FIGS. 4A-C shows analysis of root volatiles collected from potted common rue, *Ruta graveolens*, a natural source of a nematode attractant, the unusual 12 carbon terpenoid pregeijerene. This compound is unstable and degrades to geijerene at temperatures above approximately 130 C. FIG. 4A shows serious degradation when thermal desorption is used comparable to the degradation seen when common splitless injection is used as illustrated in FIG. 4B. However, degradation is minimal when on-column injection is used as illustrated in FIG. 4C in the GC/MS analyses.

Example 2

Figure 8:
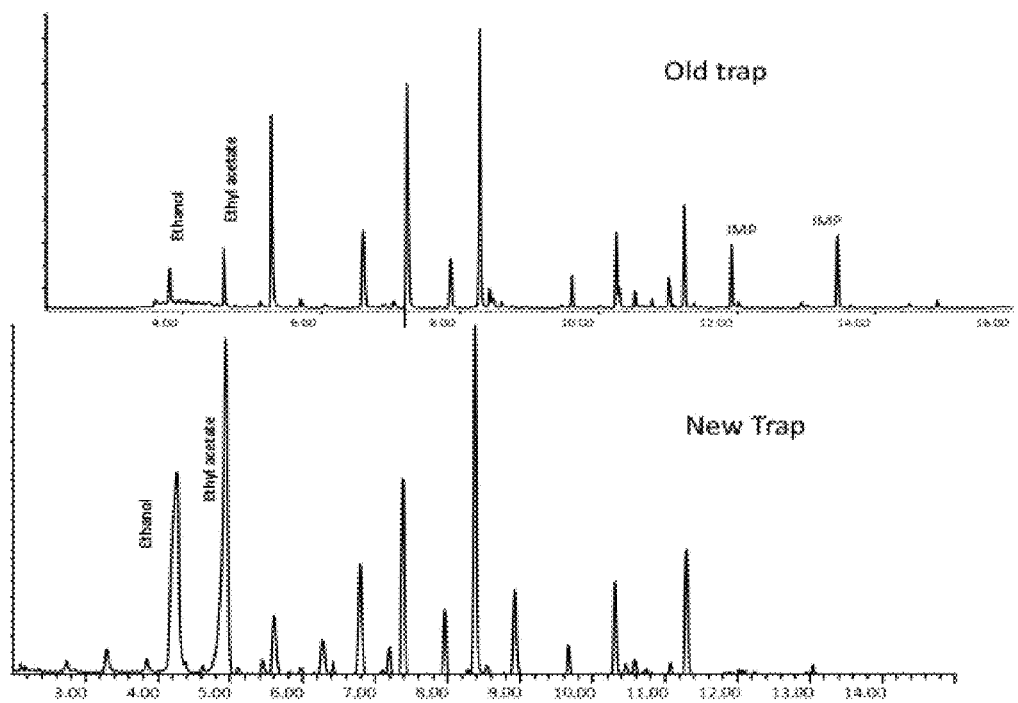
FIG. 8 is a chromatogram of Tenax collection of ripe banana volatiles analyzed using a commercial flash heated cryo trap system 30 versus the new thermal injection system 10. The significantly increased ethanol and ethyl acetate seen with the new system 10 is the consequence of better trapping and focusing. Additional more volatile compounds, including methanol, are also clearly separated on the chromatogram.

In this example, ripe banana volatiles, collected as described in Example 1, were analyzed using a commercial flash heated cryo trap system 30 (FIG. 1)(Scientific Instruments Services micro cryo-trap TD4, model 972 with controlled model 971) versus the novel injection system 10 of the claimed invention. This significantly increased ethanol and ethyl acetate seen with the novel injection system is the consequence of better trapping and focusing. More volatile compounds including methanol, are clearly separated on the chromatogram (not labeled) as depicted in FIG. 8.

Example 3

Figure 9:
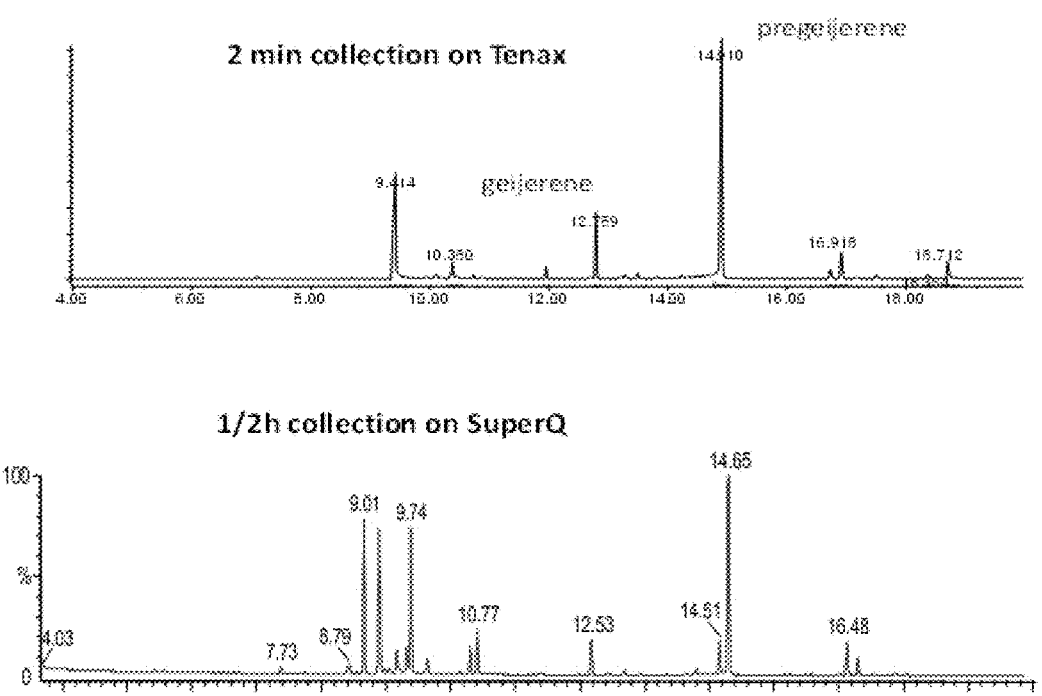
FIG. 9 is a chromatogram of citrus root volatiles collected from the same citrus tree in the field. Using either a 2 minute collection on Tenax and analyzed using GC/MS with the new thermal desorption system 10 or a ½ hour collection on the adsorbent Super Q which was then extracted with approximately 150 µl of methylene chloride followed by GC/MS analyses utilising very mild cool on column injection.
Figure 10:
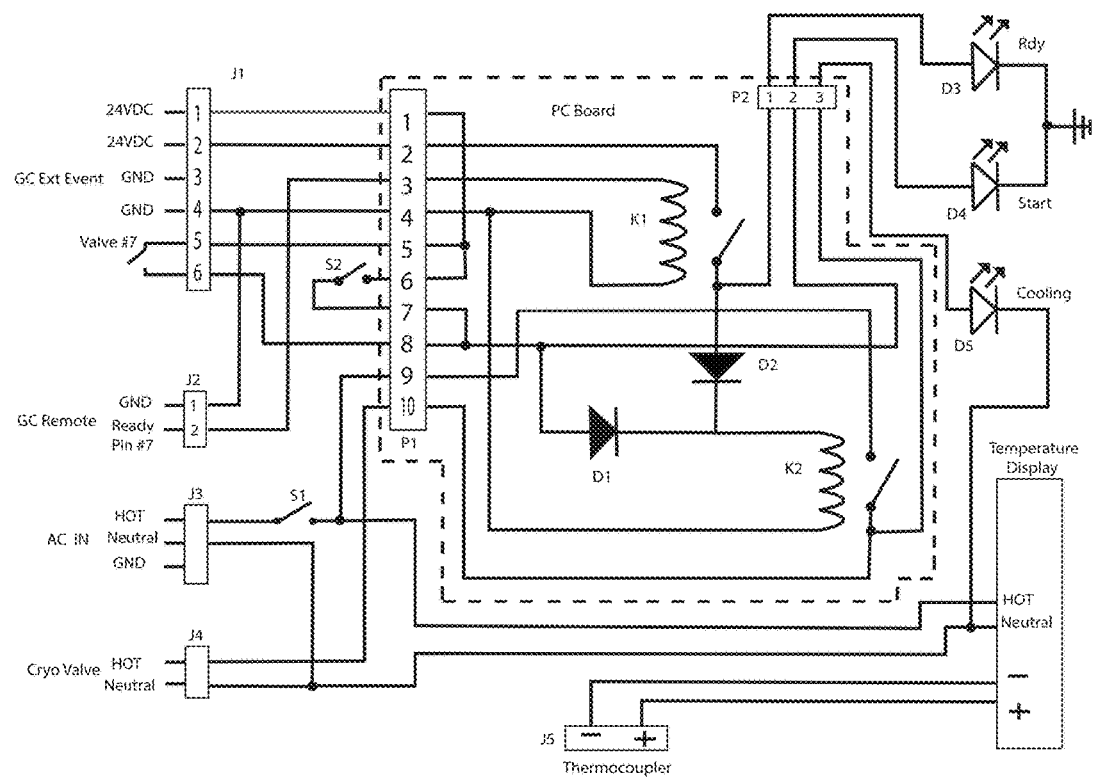
FIG. 10 is a schematic of the circuit card inside the control box 44.

Citrus root volatiles were collected from the same citrus tree in the field. An approximately ½ inch stainless steel probe especially designed for soil sampling equipped with a connector for tenax and Super Q filters (to be published) was inserted approximately 30 cm into the soil approximately 2 meters from the trunk of a tree and volatiles were collected with Super Q for approximately 30 minutes using a flow of approximately 200 ml/min by the help of a mobile battery driven vacuum pump and a flow meter with an approximately 0 to 1000 ml gas flow range (Aalborg Instruments, Orangeburg, N.Y.). The probe was then moved to the opposite side of the tree and volatiles were collected on Tenax for approximately 2 minutes under otherwise same conditions described for the Super Q collection. The Super Q was extracted with approximately 150 µl of methylene chloride and approximately 1.0µ was injected on the GC/MS using on-column injection. The Tenax collection was analyzed by the thermal desorption system 10 of the present invention at about 150 degrees C. and otherwise identical conditions. The results are shown in FIG. 9. The analyses show the same degree of degradation of pregeijerene to geijerene for both cool on column and the new thermal adsorption systems 10, probably due to a natural degradation in the soil. The additional peaks in the SuperQ collection is probably due to above ground air contamination of the sample, which is more likely to occur during longer sampling times.

It will be clear to a person skilled in the art that the scope of the present invention is not limited to the examples discussed above, but that various changes and modifications thereof are possible without departing from the scope of the invention as defined in the appended claims.

INDEX OF THE ELEMENTS

10. System for thermal Desorption
11. Split/Splitless Injector/desorption oven
14. Transfer Line
16. Adsorption Filter
18. Cryo Trap
19. Prior Art Cryo Trap
20. HE Carrier Gas inlet
22. Liquid CO2 inlet
23. CO2 Gas Outlet
24. GC Column
25. Injector Column Nut
28. Tee Male/Male/Female
29. Union Male/Male
30. Commercial cold trap with flash heating
32. Aluminum Heat Sink/Exchanger
38. Copper or Brass Insert
40. SGE/GLT Tubing
42. Restrictor for liquid CO2
44. Control Box
45. Temperature Display
46. Indicator lights
48. Control box circuit card
50. Relay K1
52. Relay K2
60. Switch S2
62. Switch S1
64. AC Main Power Connector
66. Cryo Valve Control Connector
68. GC Remote Connector
69. Thermo Coupler Temperature Sensor Connector
70. GC External Event
72. Electrical Control Valve

What is claimed is:

1. An apparatus for the analysis of volatile organic compounds in a gas chromatogram thermal desorption system, the apparatus comprising; a cryo trap directly attached to a split/splitless injector; a means of transferring desorbed compounds from said injector to a top part of a chromatographic column located inside said cryo trap, wherein said cryo trap is characterized by a low thermal mass such that the cryo trap can follow surrounding temperature changes at a rate of 5° C. per min to 10° C. per min; a restrictor portion in a liquid cooled delivery segment of the cryo trap that forces a pressure drop and cooling to occur at an end of the restrictor portion located at a bottom of the cryo trap; and wherein the split/splitless injector is configured to be used as a desorption oven and/or an injector.

* * * * *